(12) United States Patent
Wahlberg et al.

(10) Patent No.: US 10,835,664 B2
(45) Date of Patent: *Nov. 17, 2020

(54) IMPLANTABLE CELL DEVICE WITH SUPPORTIVE AND RADIAL DIFFUSIVE SCAFFOLDING

(71) Applicant: GLORIANA THERAPEUTICS SARL, Geneva (CH)

(72) Inventors: Lars Ulrik Wahlberg, Bristol, RI (US); Jens Tornøe, Ballerup (DK)

(73) Assignee: Gloriana Therapeutics, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/582,761

(22) Filed: Apr. 30, 2017

(65) Prior Publication Data

US 2017/0232186 A1 Aug. 17, 2017

Related U.S. Application Data

(63) Continuation of application No. 13/876,088, filed as application No. PCT/DK2011/050360 on Sep. 27, 2011, now Pat. No. 9,669,154.
(Continued)

(30) Foreign Application Priority Data

Sep. 27, 2010 (DK) .................. 2010 70410

(51) Int. Cl.
*A61M 5/14* (2006.01)
*C12N 5/00* (2006.01)
(Continued)

(52) U.S. Cl.
CPC .............. *A61M 5/14* (2013.01); *A61F 2/02* (2013.01); *A61F 2/022* (2013.01); *A61K 35/12* (2013.01);
(Continued)

(58) Field of Classification Search
CPC ... A61F 2/022; A61K 2035/18; A61K 9/0024; B01J 13/02; C12N 2533/30;
(Continued)

(56) References Cited

U.S. PATENT DOCUMENTS

| 5,106,627 A | 4/1992 | Aebischer et al. |
|---|---|---|
| 5,156,844 A | 10/1992 | Aebischer et al. |

(Continued)

FOREIGN PATENT DOCUMENTS

| CN | 2830410 Y | 10/2006 |
|---|---|---|
| WO | WO2006/122551 | 12/1993 |

(Continued)

OTHER PUBLICATIONS

Baron-Van Evercooren A et al., (1986), 'Schwann Cell Differentiation *in vitro*: Extracellular Matrix Deposition and Interaction,' Dev Neurosci, 8(3):182-96.

(Continued)

*Primary Examiner* — Michael L Hobbs
(74) *Attorney, Agent, or Firm* — Alan F. Feeney, Esq.; Feeney IP Law

(57) ABSTRACT

The invention comprises an implantable cell device that includes a membrane defining and enclosing a chamber; a distance body within the chamber for reducing the diffusion distance for a biological active factor to or across the membrane; and a support scaffold within the chamber for increasing the cell support surface area per unit volume of the chamber for distributing cells.

16 Claims, 10 Drawing Sheets

Related U.S. Application Data

(60) Provisional application No. 61/387,191, filed on Sep. 28, 2010.

(51) Int. Cl.
*A61F 2/02* (2006.01)
*A61M 5/00* (2006.01)
*A61K 35/12* (2015.01)
*A61L 31/00* (2006.01)
*A61L 31/04* (2006.01)
*A61L 31/16* (2006.01)

(52) U.S. Cl.
CPC ............ *A61L 31/005* (2013.01); *A61L 31/04* (2013.01); *A61L 31/16* (2013.01); *A61M 5/00* (2013.01); *C12N 5/0012* (2013.01); *A61F 2240/001* (2013.01); *A61K 2035/126* (2013.01); *A61K 2035/128* (2013.01); *A61L 2300/62* (2013.01); *A61L 2300/64* (2013.01); *Y10T 29/49826* (2015.01)

(58) Field of Classification Search
CPC ...... C12N 5/0012; C12N 5/0314; A61M 5/00; Y10T 29/49826
See application file for complete search history.

(56) References Cited

U.S. PATENT DOCUMENTS

| | | |
|---|---|---|
| 5,554,148 A | 9/1996 | Aebischer et al. |
| 5,653,687 A | 8/1997 | Mills et al. |
| 5,681,740 A | 10/1997 | Messier et al. |
| 5,773,286 A * | 6/1998 | Dionne ............... A61F 2/022 424/93.7 |
| 5,786,216 A | 7/1998 | Dionne et al. |
| 6,042,909 A | 3/2000 | Dunleavy et al. |
| 6,165,225 A | 12/2000 | Antanavich et al. |
| 6,426,214 B1 | 7/2002 | Butler et al. |
| 6,627,422 B1 | 9/2003 | Li et al. |
| 9,669,154 B2 * | 6/2017 | Wahlberg ............ A61F 2/022 |
| 2003/0124722 A1 | 7/2003 | Ohgawara et al. |

FOREIGN PATENT DOCUMENTS

| | | |
|---|---|---|
| WO | WO2009/149205 | 6/1995 |
| WO | WO1997/034586 | 9/1997 |
| WO | WO2000/058437 | 10/2000 |
| WO | WO2003/043486 | 5/2003 |
| WO | WO2010/057039 A2 | 7/2003 |
| WO | WO2004/060426 | 7/2004 |
| WO | WO2007/078922 | 10/2006 |
| WO | WO1993/024627 A1 | 7/2007 |
| WO | WO1995/017526 A1 | 12/2009 |
| WO | WO2006/026730 | 5/2010 |

OTHER PUBLICATIONS

International Search Report and Written Opinion for International Application No. PCT/DK2011/050360 dated Feb. 20, 2012 (9 pages).

* cited by examiner

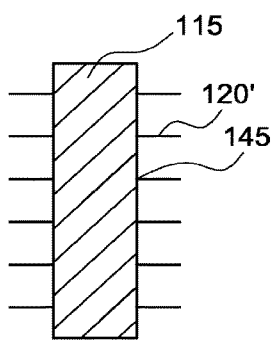
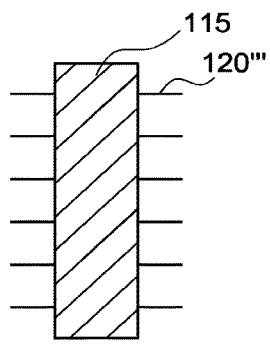
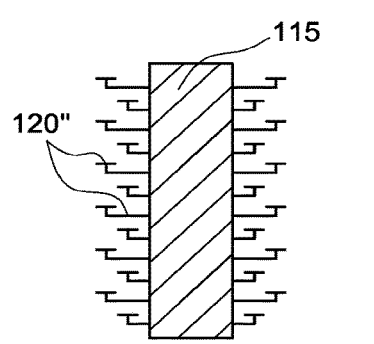
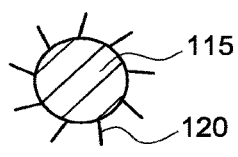
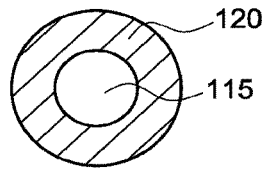
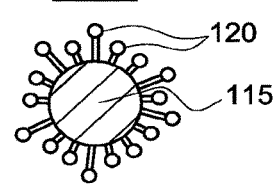
FIG. 4(a)   FIG. 4(b)   FIG. 4(c)
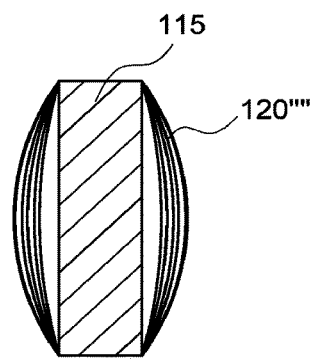
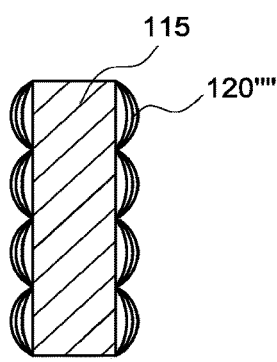
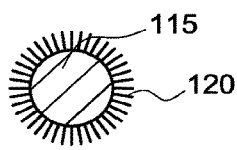
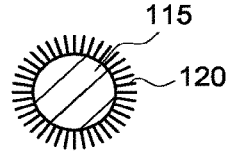
FIG. 4(d)   FIG. 4(e)

IMPLANTABLE CELL DEVICE WITH SUPPORTIVE AND RADIAL DIFFUSIVE SCAFFOLDING

CROSS-REFERENCE TO RELATED APPLICATIONS

This application is a continuation application of U.S. Ser. No. 13/876,088 filed Jun. 17, 2013 that issued as U.S. Pat. No. 9,669,154 on Jun. 6, 2017, which is the U.S. National Stage filing under 35 U.S.C. § 371 of International Application No. PCT/DK2011/050360 filed Sep. 27, 2011, which claims the benefit of Denmark Patent Application No. PA 2010 70410 filed Sep. 27, 2010 and U.S. Provisional Application No. 61/387,191 filed Sep. 28, 2010.

FIELD OF INVENTION

This present invention relates to the field of implantable medical devices. In particular, the invention relates to an implantable cell device such as a capsule with supportive and diffusive scaffolding for the treatment of diseases and disorders with encapsulated cells.

BACKGROUND OF INVENTION

Many clinical conditions, deficiencies, and disease states may be remedied or alleviated by supplying to the patient a one or more biologically active factors produced by living cells or removing from the patient deleterious factors which are metabolized by living cells. In many cases, these factors may restore or compensate for the impairment or loss of organ or tissue function. Examples of disease or deficiency states whose etiologies include loss of secretory organ or tissue function include:

(a) diabetes, wherein the production of insulin by pancreatic islets of Langerhans is impaired or lost;

(b) hypoparathyroidism, wherein the loss of production of parathyroid hormone causes serum calcium levels to drop, resulting in severe muscular tetany;

(c) Parkinsonism, wherein dopamine production is diminished; and (d) anemia, which is characterized by the loss of production of red blood cells secondary to a deficiency in erythropoietin. The impairment or loss of organ or tissue function may result in the loss of additional metabolic functions.

Accordingly, many investigators have attempted to reconstitute organ or tissue function by transplanting whole organs, organ tissue, or cells which provide secreted products or affect metabolic functions. Moreover, transplantation may provide dramatic benefits but is limited in its application by the relatively small number of organs suitable and available for grafting. In general, the patient must be immunosuppressed in order to avert immunological rejection of the transplant, which results in loss of transplant function and eventual necrosis of the transplanted tissue or cells. In many cases, the transplant must remain functional for a long period of time, even for the remainder of the patient's lifetime. It is both undesirable and expensive to maintain a patient in an immunosuppressed state for a substantial period of time.

A desirable alternative to such transplantation procedures is the implantation of cells or tissues within a physical barrier which will allow diffusion of nutrients, waste materials, and secreted products, but block the cellular and molecular effectors of immunological rejection. A variety of devices which protect tissues or cells producing a selected product from the immune system have been explored. These include extravascular diffusion chambers, intravascular diffusion chambers, intravascular ultrafiltration chambers, and implantation of microencapsulated cells. These devices would alleviate the need to maintain the patient in an immunosuppressed state. A problem with known devices is central necrosis of cells growing inside the devices. Central necrosis can occur after long-term implantation and give rise to widespread cell death inside the capsule.

A method and device for providing higher surface area per unit volume of the chamber for distributing cells and improved diffusion for delivering appropriate quantities of needed substances, such as growth factors, neuropeptides, enzymes, hormones, or other factors or, providing other needed metabolic functions, for an extended period of time would be very advantageous to those in need of long-term treatment.

Various types of cell capsules are known. For example, U.S. Pat. No. 5,786,216 discloses capsules with an inner support giving tensile strength to the device. The support may include fins extending radially along the axis of the capsule or the external surface of the inner support may be roughened or irregularly shaped. U.S. Pat. No. 6,627,422 discloses device with a mesh or yarn support for attachment of cells. WO 2006/122551 discloses an encapsulated cell device having an elongate tether comprising a stiffener to make the tether more rigid.

SUMMARY OF INVENTION

According to an embodiment of the invention, an implantable cell device is disclosed. The device includes a membrane defining and enclosing a chamber; a distance means, within the chamber, for reducing diffusion distance for a biologically active factor to/across the membrane; and a support means, within the chamber, for increasing cell support surface area per unit volume of the chamber for distributing cells.

According to another embodiment of the invention, a method for manufacturing an implantable cell device is disclosed. The method includes forming a chamber enclosed by a membrane, the chamber including a distance means for reducing diffusion distance for a biologically active factor to/across the membrane and a support means for increasing cell support surface area per unit volume of the chamber for distributing cells. Thereafter, the chamber is loaded with a population of cells, the cells being capable of secreting a biologically active factor or providing a biological function to a recipient; and lastly, the chamber is sealed.

The device of the present invention allows for a higher long term, cell survival within a mammal, such as in the brain of a mammal. By long-term according to the present invention is intended at least 6 months, such as at least 9 months, more preferably at least one year. Therefore, the implanted device is useable for long-term from the time of implantation.

BRIEF DESCRIPTION OF ACCOMPANYING DRAWINGS

The embodiments of the invention, together with its advantages, may be best understood from the following detailed description taken in conjunction with the accompanying figures in which FIG. 1 illustrates a cross-sectional view of the device according to an embodiment of the invention;

FIG. 2(A)-(E) illustrate the distance means according to various embodiments of the invention;

FIG. 3(A)-(C) illustrate cross sectional front view and top view of the distance means according to various embodiments of the invention; and FIG. 4(A)-(E) illustrate the front view and top view of the support means according to various embodiments of the invention;

DETAILED DESCRIPTION OF THE INVENTION

The invention is generally described with specific embodiments, such as distance means having a circular cross section in radial direction, positioned centrally with respect to the chamber. However, the person skilled in the art would appreciate that the invention may be practised using alternative embodiments of this invention. Furthermore, same elements of the device, in different figures, are identified with same numeral.

Figure 1:
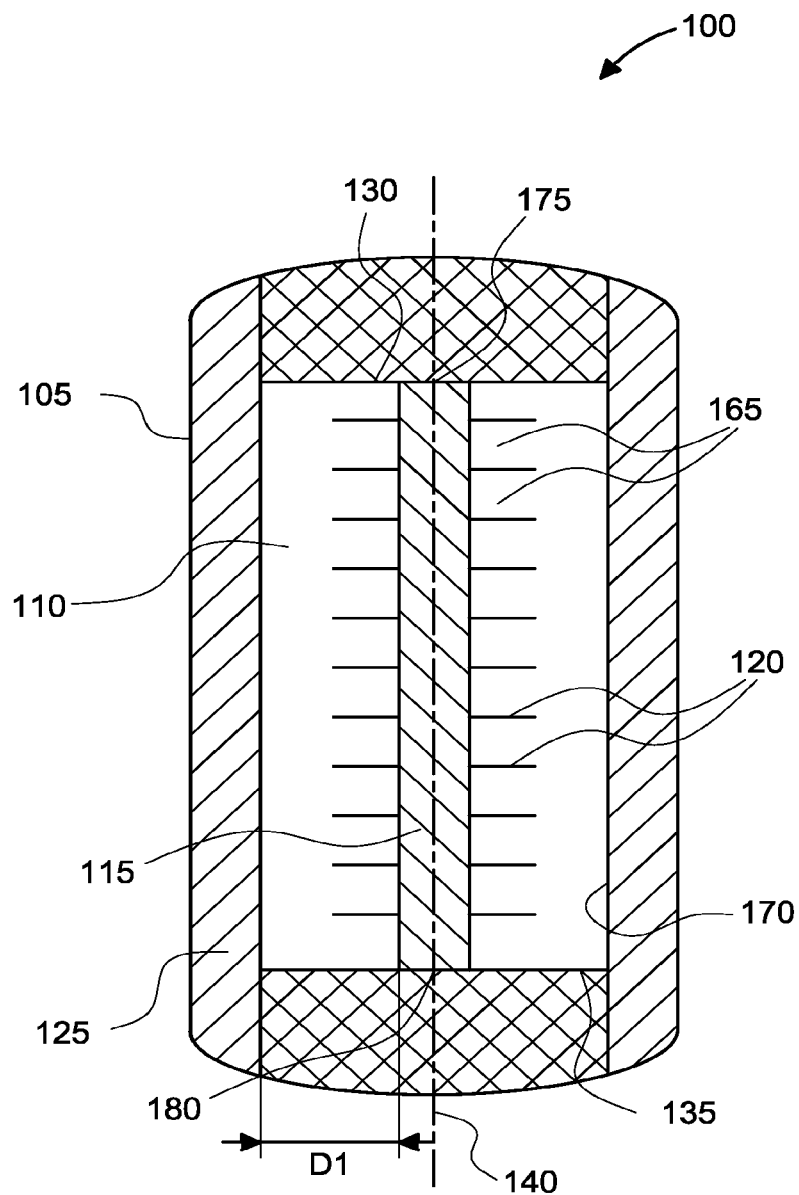

FIG. 1 illustrates a cross-sectional view of the implantable cell device according to an embodiment of the invention. The device 100 includes a membrane 105 defining and enclosing a chamber 110, a distance means 115 for reducing diffusion distance D1 for a biologically active factor to/across the membrane, and a support means 120 for increasing cell support surface area per unit volume of the chamber 110 for distributing cells. The distance means 115 and the support means 120 are both positioned within the chamber 110.

The combination of the distance means and support means results in:

a) improved, i.e. more uniform distribution of cells in the chamber, b) reduction in the number of layers of cells in any sub-compartment of the chamber, c) reduction in central necrosis, i.e. morphological changes in cells indicative of cell death in and around central section of the chamber or around the distance means, d) increasing the number of viable cells within the chamber for a specific encapsulated cell population.

Biologically Active Factor

The cells distributed within the chamber are capable of secreting a biologically active factor or providing a biological function to a recipient. The cells, in a chamber of the device, are either suspended in a liquid medium or immobilized within a hydrogel or extracellular matrix material. The types of cells that may be used in the present invention and genetic engineering of the cells for encapsulation are described in WO 2006/122551, incorporated herein by reference.

The biologically active factor is selected from a group consisting of neuropeptides, neurotransmitters, hormones, cytokines, lymphokines, enzymes, biological response modifiers, growth factors, antibodies and trophic factors.

Membrane

The device includes the membrane 105 comprising semi permeable layer 125, which defines and encloses a chamber 110. The membrane is connected to a chamber top at one end and a chamber bottom at the other end. The membrane includes at least one biocompatible semi-permeable layer 125 across which:

the biologically active factor can pass through from the chamber into surroundings such as a central nervous system; and the nutrients can pass through from the surrounding such as a central nervous system into the chamber.

A "biocompatible material" includes material that, after implantation in a host, does not elicit a detrimental host response sufficient to result in the rejection of the capsule or to render it inoperable, for example through degradation. In various embodiments of the invention, the membrane is made up of a material selected from a group consisting of polyacrylates including acrylic copolymers, polyvinylidenes, polyvinyl chloride copolymers, polyurethanes, polystyrenes, polyamides, cellulose acetates, cellulose nitrates, polysulfones including polyether sulfones, polyphosphazenes, polyacrylonitriles, poly(acrylonitrile/covinyl chloride), polytetrafluoroethylene, and derivatives, copolymers and mixtures thereof.

The thickness of the membrane is in the range of approximately 30-230 µm. The thickness is such that the membrane provides sufficient strength to the capsule for keeping the cells encapsulated and with this in mind be kept as thin as possible to take up as little space as possible.

The membrane/jacket preferably has a molecular weight cutoff of less than 1000 kD, more preferably between 50-700 kD, more preferably between 70-300 kD, more preferably between 70-150 kD, such as between 70 and 130 kD. The molecular weight cutoff should be selected to ensure that the bioactive molecule may escape from the device such as a capsule while protecting the encapsulated cells from the immune system of the patient.

The chamber defined by the membrane may include various cross-sectional shapes. In one embodiment, the cross-sectional shape of the chamber in the radial direction is circular having a diameter in the range of 220-1800 µm.

Diffusion Distance

The diffusion distance includes the distance covered within the chamber by the nutrient and biologically active factor, and is in the range of approximately 70-700 µm. The diffusion distance is defined by the maximum distance, within the chamber; a nutrient covers from an inner surface 170 of the membrane to the cells that take up the nutrient. The diffusion distance is also defined as the maximum distance the biologically active factor covers from cell(s) to the inner surface of the membrane in order to pass across the membrane into the surroundings such as a central nervous system.

The effective diffusion distance across the membrane is dependent on the thickness of the membrane, i.e. thickness of the semi-permeable layer 125. It is comprehensible that for same thickness of the membrane, reduction in the diffusion distance to the membrane reduces the effective diffusion distance as well.

Distance Means

The distance means 115 is placed within the chamber 110 and reduces the diffusion distance, in particular the maximal diffusion distance, for a biologically active factor to and across the membrane. The distance means, simultaneously reduces the maximal diffusion distance for a nutrient from inner surface (refer 170, FIG. 1) of the membrane to the cell(s).

Referring now to FIGS. 2(A)-(E) illustrating the distance means according to various embodiments of the invention.

Figures 2A, 2B:
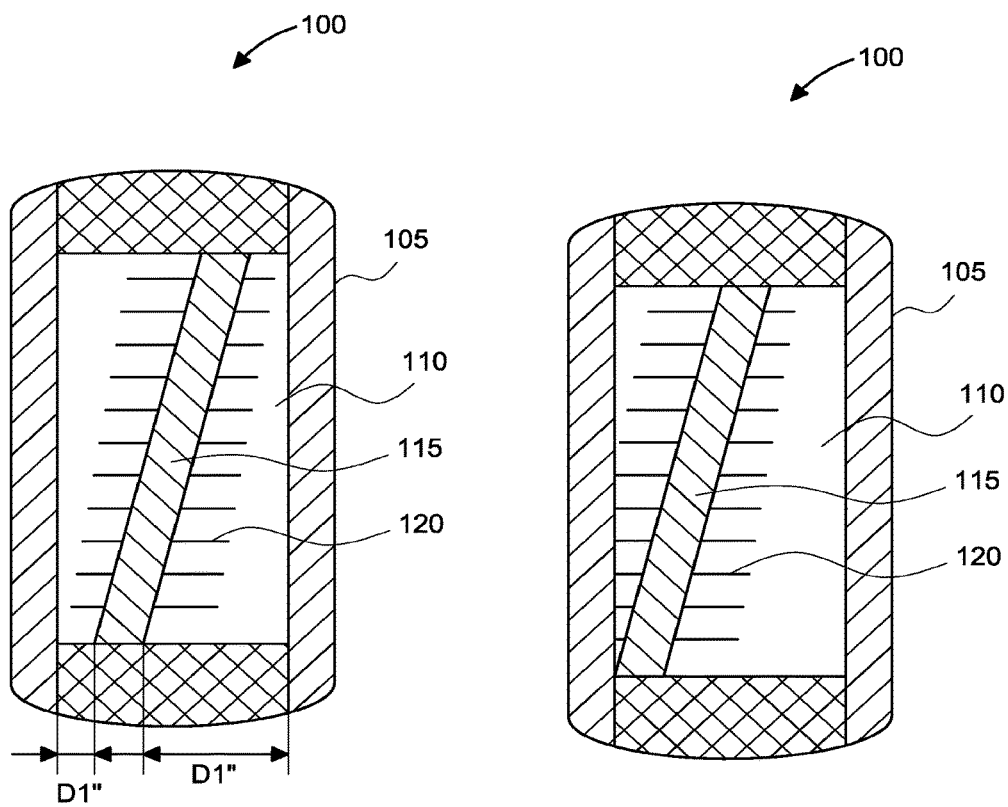
Figures 2C, 2D:
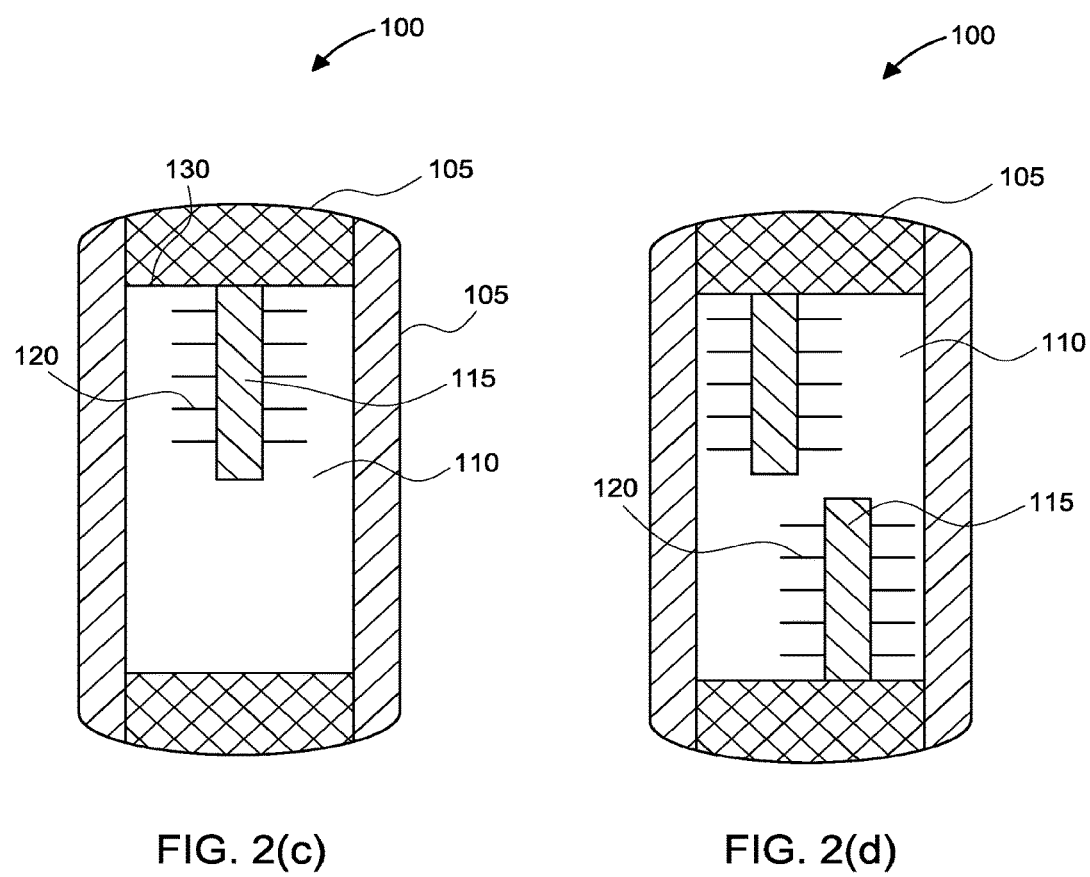
Figure 2E:
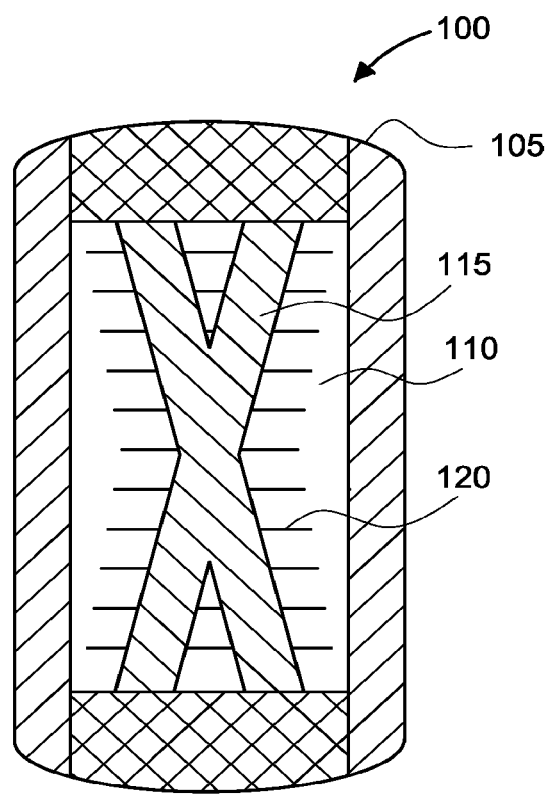

In one embodiment of the invention, the distance means 115 comprises a body such as a rod, which extends longitudinally from close to a first end (refer 175, FIG. 1) of the chamber 110 (FIGS. 2(C), (D)). In yet another embodiment of the invention, the distance means 115 comprises a body such as a rod, which extends longitudinally from close to the first end (refer 130, FIG. 1) of the chamber 110 to close or very close to a second end (refer 135, FIG. 1) of the chamber 110, as illustrated in FIGS. 2(A), (B), (E).

In many embodiments, plugs will be used to close and seal one or more ends 130, 135 of the device. The plug may suitably comprise a glue. In preferred embodiments, the distance means is secured to one or both plugs. The plugs may also be used to secure a tether 155 to the device or to secure a connection means 150, to which a tether 155 can be secured.

The glue preferably is biocompatible. In a preferred embodiment, the glue is a photo-curable glue, such as a UV curable glue, which can withstand sterilisation with radiation, chemical sterilisation or autoclaving. Examples of UV-curable glues include urethane (meth) acrylates. These are available in different blends such as urethane oligomer/acrylate monomer blends. Other suitable glues include cyanoacrylates and epoxy adhesives.

In another embodiment, the distance means (115 in FIG. 7) comprises a body made of a twisted wire with bristles (120 in FIG. 7) twisted into the wire.

In another embodiment of the invention, the distance means is placed such that at least one end of the distance means is at a centre of the cross-section of the chamber (FIGS. 1, 2(B), (C)). In yet another embodiment, the ends of the distance means are off-centre to the cross-sectional centres (refer 175 & 180, FIG. 1) of the chamber 110 (FIGS. 2(A), (D), (E)).

The distance means is placed at an angle to a longitudinal axis (refer 140, FIG. 1) of the chamber 110 (FIGS. 1, 2(A)-(E)).

The device 100 may also include a plurality of distance means 115, as illustrated in FIGS. 2(D), (E)). The plurality of distance means are placed within the chamber in a regular pattern (FIG. 2(E)) or an irregular pattern (FIG. 2(D)) and at least one of the plurality of distance means 115 comprises the support means 120.

Figure 3A:
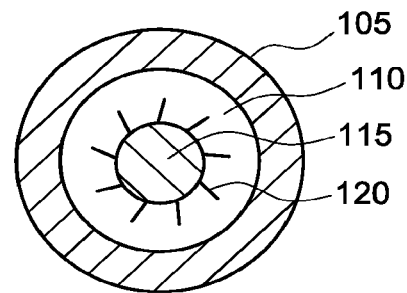
Figure 3B:
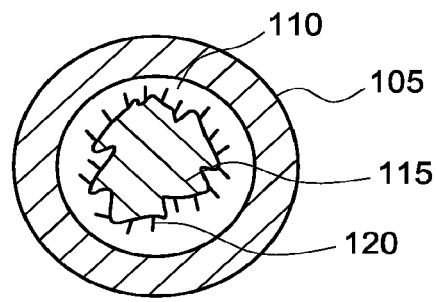
Figure 3C:
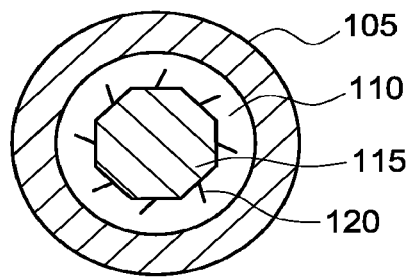

Now referring to FIGS. 3(A)-(C), which illustrate cross sectional front and top views of the distance means according to various embodiments of the invention.

The distance means includes a body such as a rod, which may include different cross-sectional shapes. In one embodiment, the distance means includes a rod having a circular cross section. The cross-sectional diameter of such a rod is in the range of approximately 30-1300 μm. Typically, the ratio of the cross-sectional diameter of the distance means with respect to the cross-section diameter of the chamber is in the range of 1:6 to close to 1:1.

In various embodiments of the invention, the cross-section of the distance means includes a shape selected from a group consisting of a regular shape (FIGS. 3(A), (C)), an irregular shape (FIG. 3(B)), a symmetrical shape (FIGS. 3(A), (C)), an asymmetrical shape (FIG. 3(B)) and a combination thereof.

In an embodiment of the invention, the distance means comprises a twisted rod. The twisted rod engages with the support means such as the bristles (described later), preferably by twisting. The twisting involves folding a length of the rod into a bent rod, usually U-shaped, with two legs. The bristles are then disposed between the two legs along a length of the bent rod. Thereafter, the two legs of the bent rod are twisted into each other along the length of the bent rod to form a twisted rod, such that that the bristles are secured between the legs of the twisted rod. The twisted rod preferably is a twisted metal wire, such as a titanium wire.

Apart from the disclosed embodiment, other options are available to secure the bristles with the distance means such as by gluing, melting, welding, flocking etc. without altering the scope of the invention. Similar methods exist in the area of interdental brushes.

It would be appreciated by the skilled person that the diffusion distance is defined by relative dimensions of a cross-section of the distance means with respect to a cross-section of the chamber. Also, the diffusion distance in a particular radial direction is defined by relative dimensions of the cross-section of the distance means with respect to the cross-section of the chamber and positioning of the distance means within the chamber.

The distance means is made up of a material, which is substantially non-toxic to cells. In various embodiments of the invention, the distance means is made up of a material selected from a group consisting of a metal such as medical grade titanium or stainless steel, an alloy such as medical grade titanium or stainless steel, a polymer such as includes acrylic, polyester, polyethylene, polypropylene, polyacetonitrile, polyethylene terephthalate, nylon, polyamides, polyurethanes, polybutester, silk, cotton, chitin, carbon and biocompatible metals and a combination thereof.

Support Means

The support means is placed within the chamber and increases cell support surface area per unit volume of the chamber for distributing cells. The support means increases the cell support area without substantially reducing the volume of the chamber. Therefore, increase in the cell support area per unit volume of the chamber and maintenance of sufficient volume of the chamber allows for having optimal population of cells in the chamber for producing the required quantity of the biologically active factor.

The support means, such as the plurality of plates 120''' and also densely spaced bristles 120' or plates 120'', result in compartmentalization of the chamber volume into discrete compartments (refer 165, FIG. 1), defined by sub-volume of the chamber. In other words, the support means 120 divides the chamber (refer 110, FIG. 1) into a plurality of compartments (refer 165, FIG. 1) defining sub-volumes within the chamber.

The compartmentalization ensures uniform distribution of cells within the chamber. The sub-volume may be defined by the volume of the chamber sandwiched between two consecutive support means. The sub-volume may also be defined by the volume of the chamber around a first support means until the sub-volume is intercepted by support means surrounding the first support means.

FIG. 4(A)-(E) illustrate the front view and top view of the support means according to various embodiments of the invention.

In one embodiment of the invention, according to FIG. 4(A), the support means 120 comprises a plurality of bristles 120' secured to the distance means 115 at at least one end 145 of the plurality of bristles 120', the plurality of bristles 120' being spread around and along at least a part of a length of the distance means 115.

In another embodiment, according to FIGS. 4(B) and (C), the support means 120 comprises a plurality of plates (120''' and 120'') secured to the distance means 115, the plurality of plates (120''' and 120'') being spread around and along at least a part of a length of the distance means 115.

In the device of FIG. 4(B), the plate may be concentric and/or non-concentric with the distance means. Furthermore, the plates 120''' may include a large plate around the distance means 115, as illustrated in FIG. 4(B) or a series of small plates 120'' spread around the distance means 115.

According to another embodiment of the invention, as illustrated in FIG. 4(D), the support means 120 includes a plurality of filaments 120'''' with a first end of the plurality of filaments 120'''' secured close to a first end and a second end of the plurality of filaments 120'''' close to a second end of the distance means 115, the plurality of filaments 120'''' being spread around and along a length of the distance means 115. In yet another embodiment of the invention, the support means 120 comprises a plurality of filaments 120'''', wherein a first end and a second end of the plurality of the filaments 120'''' are secured to the distance means 115 at different locations along a length of the distance means 115, as illustrated in FIG. 4(E). The filament is selected from a group consisting of twisted yarns and woven mesh tubes.

The support means may include a coating of a cell-adhesive agent or cell viability enhancing substance. The support means may also include a cell-adhesive agent or cell viability enhancing substance, which is co-extruded with the distance means 115.

Figure 5:
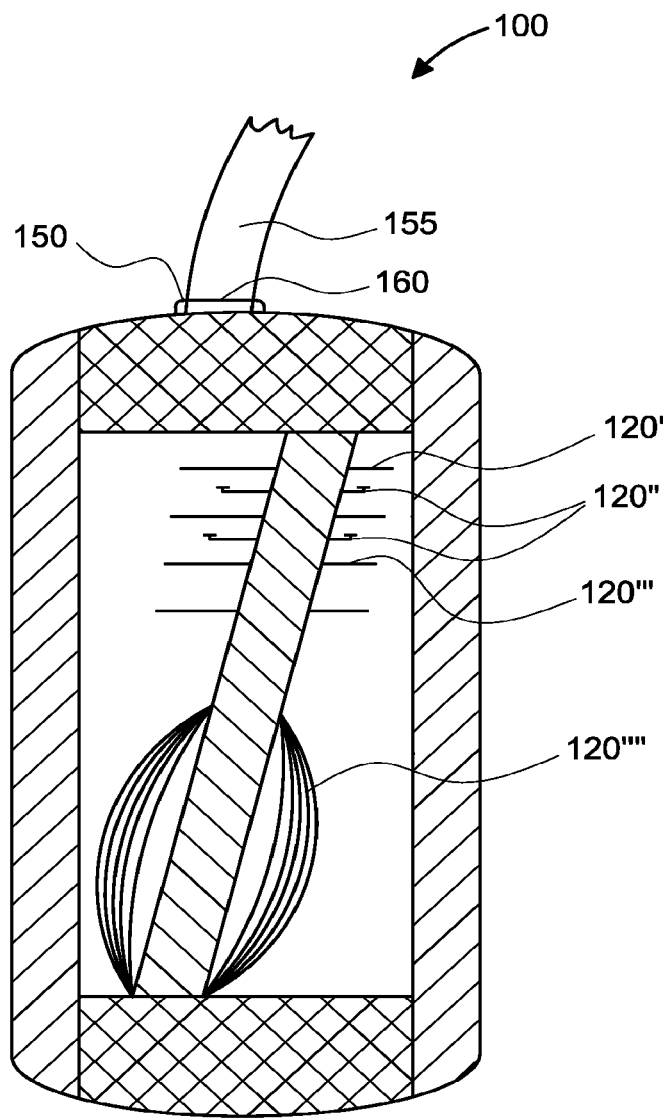
FIG. 5 illustrates a distance means with a combination of various support means along with a tether according to an embodiment of the invention.

In other embodiment of the invention, the support means may include a combination of support means 120 along and spread around the distance means 115, wherein the support means is selected from a group consisting of support means 120', 120'', 120''', 120'''', and 120''''', as illustrated in FIG. 5.

The support means is made up of a biocompatible, substantially non-degradable material. The material is selected from a group consisting of acrylic, polyester, polyethylene, polypropylene, polyacetonitrile, polyethylene terephthalate, nylon, polyamides, polyurethanes, polybutester, silk, cotton, chitin, carbon and biocompatible metals.

A person skilled in the art would appreciate that the support means such as plurality of bristles and plurality of plates provide radial cell support between the distance means and the membrane. Therefore, in combination with the distance means, such support means not only reduces the maximum diffusion distance but also substantially eliminates any barrier that the nutrient may encounter while diffusing towards the distance means or the biologically active factor may encounter while diffusing away from the distance means. It is apparent that substantially eliminating the barrier in the diffusion of the nutrients or biologically active factor would result in improved diffusion, reduced competition among the cells for nutrients and reduced central necrosis.

Dimensions

Figure 6:
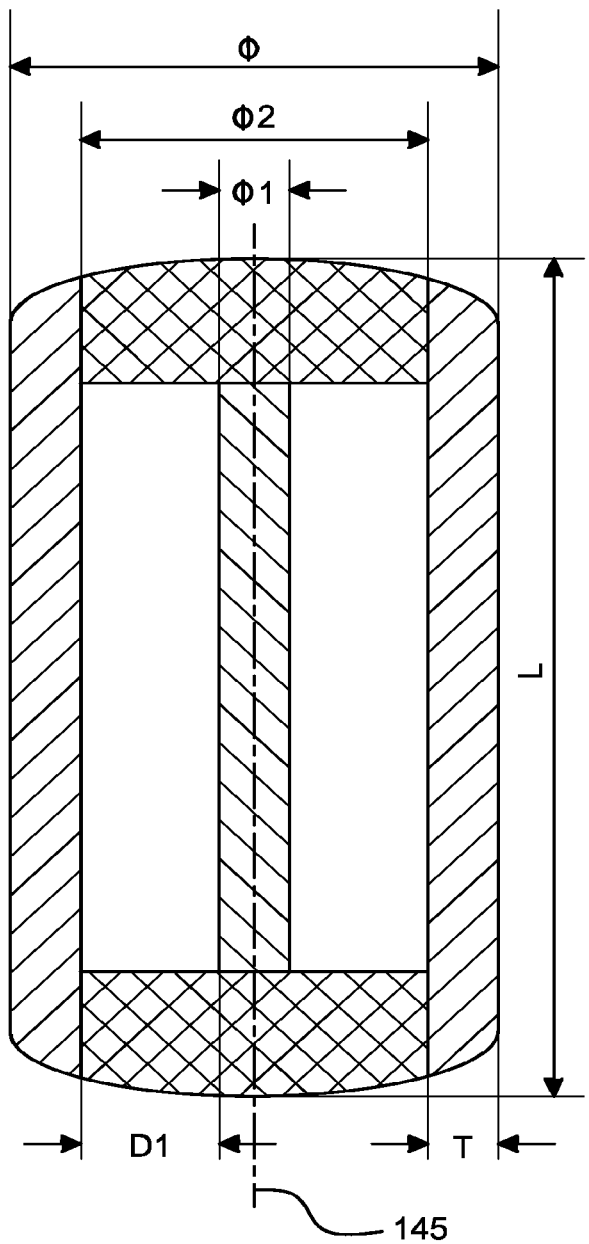
FIG. 6 illustrates the device with dimensions of different elements of the device according to an embodiment of the invention.

FIG. 6 illustrates the device with dimensions of different elements of the device according to an embodiment of the invention.

The distance means 115 includes a circular cross-section in the radial direction and has a diameter $\Phi 1$ in the range of approximately 30-1300 μm. The chamber 110 includes a circular cross-section in the radial direction and has a diameter $\Phi 2$ in the range of approximately 220-1800 μm. In an embodiment, the ratio of the diameter $\Phi 1$ of the distance means 115 having circular cross-section relative to the diameter $\Phi 2$ of the chamber 110 having circular cross section is in the range of approximately 1:6 to close to 1:1.

The diffusion distance D1 is typically in the range of approximately 70-700 μm and the thickness T of the membrane 125 is in the range of approximately 30-230 μm.

The device 100 is typically an elongated cylindrical capsule, where the diameter $\Phi$ of the cylinder is in the range of approximately 320-2300 μm and length L of the elongated capsule is in the range of approximately 3-60 mm.

Method for Manufacturing

The invention relates to a method for manufacturing the implantable cell device 100, the method includes forming a chamber 100 enclosed by a membrane 125, the chamber comprising a distance means 115 for reducing diffusion distance for a biologically active factor to/across the membrane 125 and a support means 120 for increasing cell support surface area per unit volume of the chamber 110 for distributing cells. Thereafter, loading the chamber 110 with a population of cells, the cells being capable of secreting a biologically active factor or providing a biological function to a recipient; and sealing the chamber 110.

In an embodiment, the implantable cell device is manufactured by assembling a number of components using tools designed for this purpose. Initially, all components are cleaned thoroughly to remove particulates associated with component manufacturing. Using a hub/fill port as starting point, a load tube is glued to the hub to allow injected cells to enter through the hub and load tube into the finished device. The hollow fibre membrane is glued to the distal end of the load tube, and the scaffold material is subsequently inserted into the hollow fibre. Alternatively, the scaffold material is inserted in the fibre before gluing to the load tube. Finally, the end of the hollow fibre membrane distal to the load tube is closed by gluing, thereby sealing the device. Alternatively, a tether is attached to the device by means of a linker attached to both the tether and device. In one embodiment, a cylindrical tether tube is glued to the membrane by means of a titanium linker glued to both the tether and membrane.

Figure 8:
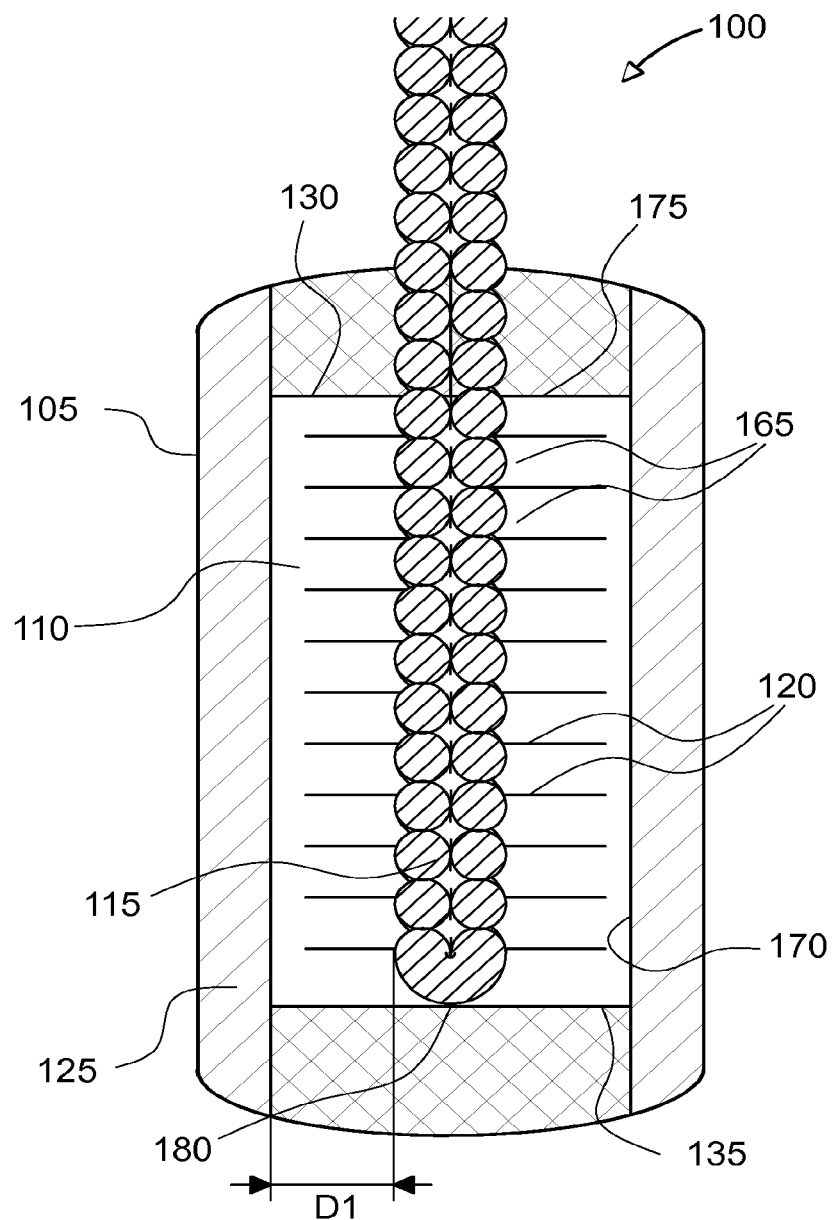
FIG. 8 illustrates the device wherein the distance means, here a twisted wire, protrudes through the end closure to serve as a linker to be attached to a non-illustrated tether tube.

Instead of using a titanium linker, the distance means 115 can be made to protrude through the end glue seal to function as a linker for attachment of a cylindrical tether tube to the device as illustrated in FIG. 8. The assembled devices are sterilized, e.g. by autoclaving, chemical sterilisation or irradiation before cell filling.

In one embodiment, the distance means 115 is placed in the chamber 110 such that the distance means 115 is secured to close to a first end 175 of the chamber 110. In another embodiment, the distance means 115 is placed in the chamber 110 such that a first end of the distance means 115 is secured close to a first end 175 of the chamber 110 and a second end of the distance means 115 is secured close to a second end 180 of the chamber 110. In another embodiment, the distance means 115 is made to protrude from the first end 175 or second end 180 to function as a linker to a cylindrical tether tube. In other embodiments, the distance means 115 is placed such that at least one end of the distance means is at a centre of the cross-section of the chamber 110; or the ends of the distance means 115 are off-centre to the cross-sectional centres of the chamber 110. The distance means is placed at an angle to a longitudinal axis of the chamber.

In an embodiment, the support means 120 comprising a plurality of bristles 120' secured to the distance means 115 at at least one end of the plurality of bristles 145; and the plurality of bristles 120' are spread around and along at least a part of a length of the distance means 115.

In another embodiment, the support means 120 comprising a plurality of plates 120''/120''' are secured to the distance means 115; and the plurality of plates 120″/120‴ are spread around and along at least a part of a length of the distance means 115.

In yet another embodiment, the support means 120 comprising a plurality of filaments 120‴ are secured with a first end of the plurality of filaments 120″″ close to a first end of the distance means 115 and a second end of the plurality of filaments 120″″ close to a second end of the distance means 115; and the plurality of filaments 120″″ are spread around and along a length of the distance means 115.

In yet another embodiment, the support means 120 comprising a plurality of filaments 120″″ are secured to the distance means 115 such that a first end and the second end of the plurality of the filaments 120″″ are secured at different locations along a length of the distance means 115.

The support means 120 may be coated with a cell-adhesive agent or cell viability enhancing substance. In another embodiment, the support means 120 comprising a cell-adhesive agent or cell viability enhancing substance are co-extruded with the distance means.

According to an embodiment, a plurality of distance means 115 are placed within the chamber 110 in a regular pattern or an irregular pattern, wherein at least one of the plurality of the distance means 115 comprises the support means 120.

The device 100 may further be provided with a connecting means 150 for connecting with a distal end 160 of an elongated tether 155.

The method includes manufacturing steps to include other features of the device.

Other Embodiments of the Invention

Implantable Means

According to FIG. 5, the device 100 includes a connecting means 150 for connecting the device 100 with a distal end 160 of an elongated tether 155.

A vehicle for positioning the cell device includes the cell device 100 and the tether 155 that extends from the capsule and which is of a length sufficient to reach at least from the treatment site to the proximity of the insertion site thereby facilitating fixation of the capsule at the insertion site, e.g. to the outer surface of the skull. The insertion site is subsequently covered by skin. In an alternative approach, the cannula is removed prior to the insertion of the capsule into the treatment site.

In an embodiment, to facilitate that the cell device may be pushed into the treatment site by use of the tether, it may be necessary to stiffen the tether, e.g. by locating a small diameter wire portion of the pusher into a hollow cavity of the tether.

To ensure that the cell device is placed accurately at the treatment site; it is desired that when the device is being pushed into the treatment site, the device maintains an acceptable level of resistance against deformation under the compressive stress conditions of pushing such as when the device is subjected to a uniaxial compressive stress. When the device is being pushed, such resistance restricts significant or any deformation of the device such as restricting spreading of the device in a radial or lateral direction. The distance means, included in the device, provides enough resistance against deformation such that the device attains an effective resistance against significant or any deformation when the device is subjected to the compressive stress of pushing, thereby allowing an accurate and reliable positioning of the device at the treatment site. It is comprehensible that for same compressive stress condition, the effective resistance against significant or any deformation of the device with the distance means included therein is substantially higher than the resistance against such deformation if the distance means was not included in the cell device.

It is also desired that the device does not bend when being pushed into the treatment site. The distance means also serves to provide the device with a higher degree of stiffness and resistance against bending.

Storage Container

Cell devices with or without tethers of the kind known from the prior art have been stored and shipped in storage containers of the kind described in U.S. Pat. No. 5,681,740. The containers have securing means that secure the capsule and/or the tether to the bottom of the container. The securing means serve to avoid undue contact between the device and other components. The securing means have a smaller diameter than the device/tether to secure the capsule in position in several places.

In an embodiment, the device comprising the cells is stored in the storage container (not shown) having an opening into a container cavity for storing the device immersed in a fluid medium, and a closure for closing the opening, the closure comprising fixation means for attaching the device to the closure.

The container may form an elongated cavity extending along the longitudinal axis 140 for storing of the device in an elongated outstretched condition. Other inner shapes of the container are conceivable depending on the dimensions of the therapy system.

The closure may comprise a fixation member of a resilient material and provided with an opening dimensioned to narrowly surround a gripped portion of the device thereby to detachably attach the device to the closure. Preferably, the fixation member forms part of a seal provided between the container and the closure to facilitate antibacterial storage of the implantable cell device. Additionally, the closure may comprise an outer surface with fixation means for attaching a separate handle to the closure.

Encapsulated Cell Therapy

The cell device such as a capsule, in the following referred to as the capsule, has a membrane which is tailored to control diffusion of molecules, such as growth factor hormones, neurotransmitters, peptides, antibodies and complements, based on their molecular weight or size. Using encapsulation techniques, cells can be transplanted into a host without immune rejection, either with or without use of immunosuppressive drugs. Useful biocompatible polymer capsules usually contain a core/chamber that contains cells, either suspended in a liquid medium or immobilised within an immobilising matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule/factor of interest to easily diffuse from the capsule into the surrounding host tissue and allows nutrients to diffuse easily into the capsule and support the encapsulated cells. The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. The capsules allow for the passage of metabolites, nutrients and therapeutic substances while minimizing the detrimental effects of the host immune system. Components of the biocompatible material may include a surrounding semipermeable membrane and the internal cell-supporting scaffolding/support means. Preferably, the recombinant cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fibre structures may be used for cell implantation. Biodegradable polymers include those comprised of poly(lactic acid) PLA, poly(lactic-coglycolic acid) PLGA, and poly(glycolic acid) PGA and their equivalents. Foam scaffolds may be used to provide surfaces onto which transplanted cells may adhere. Woven mesh tubes may be used as vascular grafts. Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

The membrane/jacket preferably has a molecular weight cutoff of less than 1000 kD, more preferably between 50-700 kD, more preferably between 70-300 kD, more preferably between 70-150 kD, such as between 70 and 130 kD. The molecular weight cutoff should be selected to ensure that the bioactive molecule may escape from the capsule while protecting the encapsulated cells from the immune system of the patient.

Various polymers and polymer blends can be used to manufacture the surrounding semipermeable layer includes polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers, poly(acrylonitrile/covinyl chloride) (Pan-PVC) and mixtures thereof. Preferably, the surrounding semipermeable membrane is a biocompatible semipermeable hollow fibre membrane.

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations, which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. A particularly preferred shape is cylinder-shaped as such a shape is easily produced from hollow fibres which can be produced industrially. When macrocapsules are used, preferably at least $10^3$ cells are encapsulated, such as between $10^3$ and $10^8$ cells are encapsulated, most preferably $10^4$ to $10^6$ cells are encapsulated in each device. Of course, the number of cells in each capsule depends on the size of the capsule. As a rule of thumb, in a capsule with distance and support means of this invention, between approximately 5,000 and 50,000 cells per μl of capsule (volume calculated as the volume of the chamber including distance means and support), more preferably from 10,000 to 40,000 cells per μL, more preferably from 20,000 to 30,000 cells per μl may be loaded. The number of cells to be loaded also depends on the size of the cells.

Dosage may be controlled by varying the dimensions (length, diameter) of the capsule and/or by implanting a fewer or greater number of capsules, preferably between 1 and 10 capsules per patient.

The scaffolding/support means may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method may also be used, as described, e.g., in U.S. Pat. No. 5,653,687, incorporated by reference.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see WO 97/34586, incorporated by reference).

Foam Scaffolds/Support Means The foam scaffold may be formed from any suitable material that forms a biocompatible foam with an open cell or macroporous structure with a network of pores. An open-cell foam is a reticulate structure of interconnected pores. The foam scaffold provides a non-biodegradable, stable scaffold material that allows attachment of adherent cells. Among the polymers that are useful in forming the foam scaffolds for the devices of this invention are thermoplastics and thermoplastic elastomers.

Some examples of thermoplastic materials useful in forming suitable foam scaffolds are: acrylic, modacrylic, polyamide, polycarbonate, polyester, polyethylene, polypropylene, polystyrene, polysulfone, polyethersulfone and polyvinylidene fluoride. Some examples of elastomer materials useful in forming suitable foam scaffolds are: polyamide polyester, polyethylene, polypropylene, polystyrene, polyurethane, polyvinyl alcohol, polyethylene vinylacetate, and silicone.

Thermoplastic foam scaffolds made from polysulfone and polyethersulfone, and thermoplastic elastomer foam scaffolds made from polyurethane and polyvinyl alcohol are preferred.

The foam must have some (but not necessarily all) pores of a size that permits cells to attach to the walls or surfaces within the pores. The pore size, pore density and void volume of the foam scaffold may vary. The pore shape may be circular, elliptical or irregular. Because the pore shape can vary considerably, its dimensions may vary according to the axis being measured. For the purposes of this invention, at least some pores in the foam should have a pore diameter of between 20-500 μm, preferably between 50-150 μm. Preferably the foregoing dimensions represent the mean pore size of the foam. If non-circular, the pore may have variable dimensions, so long as its size is sufficient to permit adherent cells to attach to the walls or surfaces within the pore. In one embodiment, foams are contemplated having some elliptical pores that have a diameter of 20-500 µm along the minor axis and a diameter of up to 1500 µm along the major axis of the elliptical pores.

In addition to the foregoing cell permissive pores sizes, preferably a least a fraction of the pores in the foam should be less than 10 µm to be cell impermissive but still provide channels for transport of nutrients and biologically active molecules throughout the foam.

Pore density of the foam (i.e., the number per volume of pores that can accommodate cells, as described above) may vary between 20-90%, preferably between 50-70%.

Similarly, the void volume of the foam may vary between 20-90%, preferably between 30-70%.

The walls or surfaces of the pores may be coated with an extracellular matrix molecule or molecules, or other suitable molecule. This coating can be used to facilitate adherence of the cells to the walls of the pores, to hold cells in a particular phenotype and/or to induce cellular differentiation.

Preferred examples of extracellular matrix molecules (ECM) that can be adhered to the surfaces within the pores of the foams include: collagen, laminin, vitronectin, poly-ornithine and fibronectin. Other suitable ECM molecules include glycosaminoglycans and proteoglycans; such as chrondroitin sulfate, heparin sulfate, hyaluron, dermatan sulfate, keratin sulfate, heparan sulfate proteoglycan (HSPG) and elastin.

The ECM may be obtained by culturing cells known to deposit ECM, including cells of mesenchymal or astrocyte origin. Schwann cells can be induced to synthesize ECM when treated with ascorbate and cAMP. See, e.g., Baron-Van Evercooren et al., "Schwann Cell Differentiation in vitro: Extracellular Matrix Deposition and Interaction," Dev. Neurosci., 8, pp. 182-96 (1986).

In addition, adhesion peptide fragments, e.g., RGD containing sequences (ArgGlyAsp), YIGSR-containing sequences (TyrIleGlySerArg), as well as IKVAV containing sequences (IleLysValAlaVal), have been found to be useful in promoting cellular attachment. Some RGD-containing molecules are commercially available—e.g., PepTite-2000™ (Telios).

The foam scaffolds of this invention may also be treated with other materials that enhance cellular distribution within the device. For example, the pores of the foam may be filled with a non-permissive hydrogel that inhibits cell proliferation or migration. Such modification can improve attachment of adherent cells to the foam scaffold. Suitable hydrogels include anionic hydrogels (e.g., alginate or carageenan) that may repel cells due to charge. Alternately, "solid" hydrogels (e.g., agarose or polyethylene oxide) may also be used to inhibit cell proliferation by discouraging binding of extracellular matrix molecues secreted by the cells.

Treatment of the foam scaffold with regions of a non-permissive material allows encapsulation of two or more distinct cell populations within the device without having one population overgrow the other. Thus non-permissive materials may be used within the foam scaffold to segregate separate populations of encapsulated cells. The distinct populations of cells may be the same or different cell types, and may produce the same or different biologically active molecules. In one embodiment, one cell population produces a substance that augments the growth and/or survival of the other cell population. In another embodiment, multiple cell types producing multiple biologically active molecules are encapsulated. This provides the recipient with a mixture or "cocktail" of therapeutic substances. The devices of this invention may be formed according to any suitable method. In one embodiment, the foam scaffold may be pre-formed and inserted into a pre-fabricated jacket, e.g., a hollow fibre membrane, as a discrete component.

Any suitable thermoplastic or thermoplastic elastomer foam scaffold material may be preformed for insertion into a pre-fabricated jacket. In one embodiment we prefer polyvinyl alcohol (PVA) sponges for use as the foam scaffold. Several PVA sponges are commercially available. For example, PVA foam sponges # D-3, 60 µm pore size are suitable (Rippey Corp, Kanebo). Similarly, PVA sponges are commercially available from Ivalon Inc. (San Diego, Cailf.) and Hydrofera (Cleveland, Ohio). PVA sponges are water-insoluble foams formed by the reaction of aerated Polyvinyl alcohol) solution with formaldehyde vapor as the cross-linker. The hydroxyl groups on the PVA covalently crosslink with the aldehyde groups to form the polymer network. The foams are flexible and elastic when wetted and semi-rigid when dried.

The filaments used to form the yarn or mesh internal scaffold are formed of any suitable biocompatible, substantially non-degradable material. Materials useful in forming yarns or woven meshes include any biocompatible polymers that are able to be formed into fibres such as, for example, acrylic, polyester, polyethylene, polypropylene, polyacrylonitrile, polyethylene terephthalate, nylon, polyamides, polyurethanes, polybutester, or natural fibres such as cotton, silk, chitin or carbon. Any suitable thermoplastic polymer, thermoplastic elastomer, or other synthetic or natural material with fibre-forming properties may be inserted into a pre-fabricated hollow fibre membrane or a hollow cylinder formed from a flat membrane sheet. For example, silk, PET or nylon filaments used for suture materials or in the manufacture of vascular grafts are highly conducive to this type of application. In other embodiments, metal ribbon or wire may be used and woven. Each of these filament materials has well-controlled surface and geometric properties, may be mass produced, and have a long history of implant use. In certain embodiments, the filaments may be "texturized" to provide rough surfaces and "hand-holds" onto which cell projections may attach. The fila0ments may be coated with extracellular matrix molecules or surface-treated (e.g. plasma irradiation or NaOH or KOH etching) to enhance cellular adhesion to the filaments.

In one embodiment, the filaments, preferably organized in a non-random unidirectional orientation, are twisted in bundles to form yarns of varying thickness and void volume. Void volume is defined as the spaces existing between filaments. The void volume in the yarn should vary between 20-95%, but is preferably between 50-95%. The preferred void space between the filaments is between 20-200 µm, sufficient to allow the scaffold to be seeded with cells along the length of the yarn, and to allow the cells to attach to the filaments. The preferred diameter of the filaments comprising the yarn is between 5-100 µm. These filaments should have sufficient mechanical strength to allow twisting into a bundle to comprise a yarn. The filament cross-sectional shape can vary, with circular, rectangular, elliptical, triangular, and star-shaped cross-section being preferred.

Figure 7:
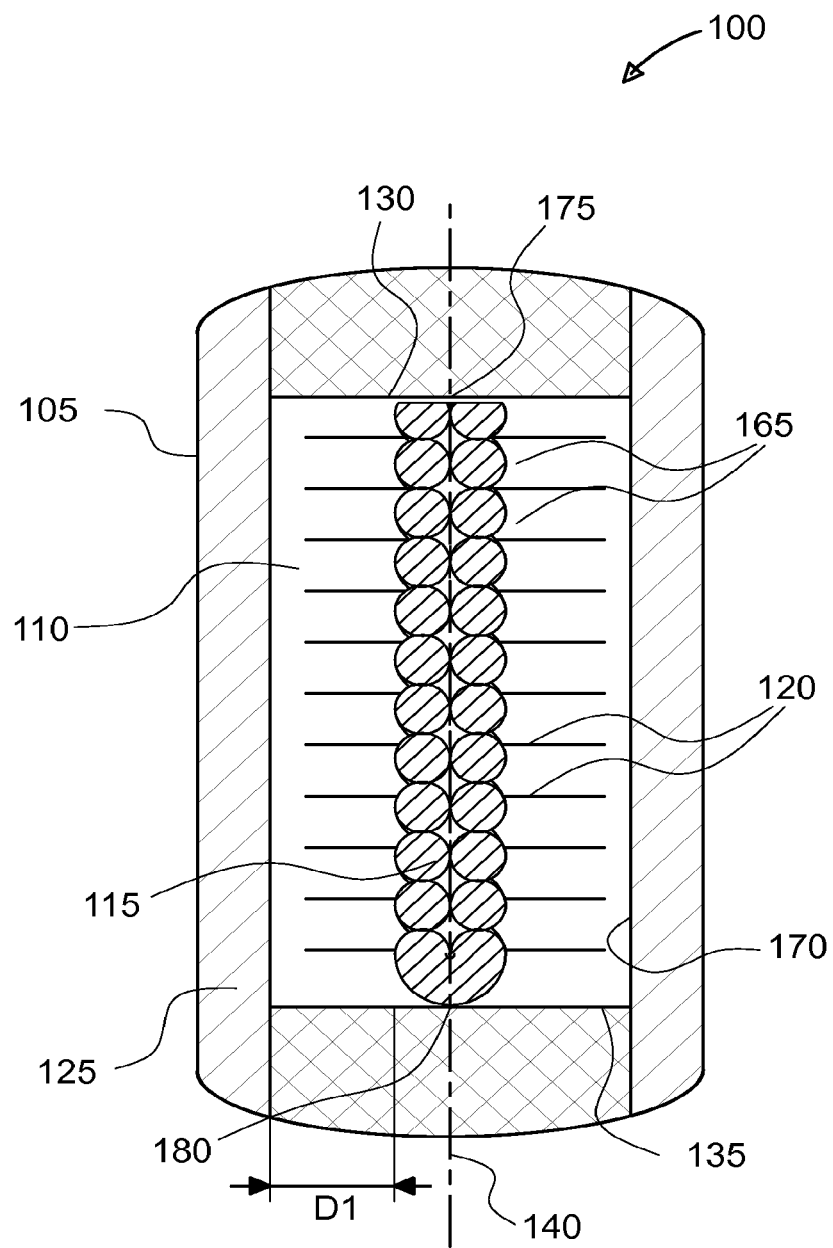
FIG. 7 illustrates the device with a twisted wire as distance means and support means in the shape of bristles. Together the twisted wire and bristles define a brush scaffolding.

In another embodiment illustrated in FIG. 7, the filaments or yarns 120 are used as bristles in a brush scaffold, for example as a twisted wire brush 115. The twisted wire core 115 is made from a biocompatible material such as implantation grade titanium. Lengths of filament or yarn 120 are distributed along a length of wire which is bent back over the lengths of filament or yarn and twisted by rotation to fix the filament or yarn bristles. The bristles are cut to length to obtain a brush diameter suitable for insertion into the membrane. Within the membrane 125, the twisted wire core serves to keep the bristles separated and fixed within the device, to strengthen the device, and to serve as a distance means to decrease the diffusion distance within the device. As illustrated in FIG. 8, the twisted wire core can also be made to protrude from a device end to serve as a linker to an attached cylindrical tether tube.

In another embodiment, the filaments or yarns are woven into a mesh. The mesh can be produced on a braider using carriers, similar to bobbins, containing monofilaments or multifilaments, which serve to feed either the yarn or filaments into the mesh during weaving. The number of carriers is adjustable and may be wound with the same filaments or a combination of filaments with different compositions and structures. The angle of the braid, defined by the pick count, is controlled by the rotational speed of the carriers and the production speed. In one embodiment, a mandrel is used to produce a hollow tube of mesh. In certain embodiments, the braid is constructed as a single layer, in other embodiments it is a multi-layered structure. The tensile strength of the braid is the linear summation of the tensile strengths of the individual filaments.

Examples of suitable monofilaments for use in the present invention are found in U.S. Pat. No. 6,627,422. One example is a PET yarn which is woven into a braid. This PET braid was constructed from a 34 strand, 44 denier multifilament yarn woven onto a 760 μm O. D. mandrel with a 16 carrier braider at a pick count of 20 picks per inch (ppi). The PET yarn may also be used in non-woven strands. Another example is nylon monofilaments woven into a braid. This nylon braid was constructed from a 13 strand, 40 denier multifilament yarn woven onto a 760 μm O. D. mandrel with a 16 carrier braider at a pick count of 18 ppi. A further example includes stainless steel multifilaments woven into a braid. This stainless steel braid was constructed from a ribbon woven onto a 900 μm O. D. mandrel with a 16 carrier braider at a pick count of 90 ppi. The tensile strength of these PET, nylon, and stainless steel braids was 2.7, 2.4, and 3.6 kg force at break, respectively.

In one embodiment, a tubular braid is constructed. In an additional embodiment, the braid is inserted into a hollow fibre membrane. In a further embodiment, cells are seeded onto the hollow fibre membrane. In an additional embodiment, the cells are allowed to infiltrate the wall of the mesh tube to maximize the surface area available for cell attachment. In this embodiment, the braid serves both as a cell scaffold matrix and as an inner support for the device. The increase in tensile strength for the braid-supported device is significantly higher than in alternative approaches.

It is important to note that the Figures illustrate specific applications and embodiments of the invention, and it is not intended to limit the scope of the present disclosure or claims to that which is presented therein. Throughout the foregoing description, for the purposes of explanation, numerous specific details, such as circular cross section distance means, centrally positioned distance means, support means as bristles, etc., were set forth in order to provide a thorough understanding of the invention. It will be apparent, however, to one skilled in the art that the invention may be practised without some of these specific details and by employing different embodiments in combination with one another. The underlying principles of the invention may be employed using a virtually unlimited number of different combinations.

Accordingly, the scope of the invention should be judged in terms of the claims which follow.

The invention claimed is:

1. An implantable cell device comprising:
a membrane defining and enclosing a chamber;
a twisted wire or twisted rod as a distance means, within the chamber, for reducing diffusion distance for a biologically active factor to/across the membrane; and
bristles attached to said twisted wire or twisted rod as support means, within the chamber, for increasing cell support surface area per unit of volume of the chamber for distributing cells,
wherein increased cell support surface area allows increased cell viability for at least six months when implanted inside of a living creature;
wherein said twisted wire or twisted rod and said bristles form a brush scaffolding;
wherein the twisted wire or twisted rod includes a cross-section having a diameter in the range of approximately 5-1000 pm, the chamber has a circular cross-section having a diameter in the range of approximately 250-1500 pm, the device is an elongated cylindrical capsule with a diameter in the range of approximately 350-2000 μm and a length in the range of 5-50 mm.

2. The device according to claim 1, wherein the cells are capable of secreting a biologically active factor or providing a biological function to a recipient.

3. The device according to claim 2, wherein the biologically active factor is selected from a group consisting of neuropeptides, neurotransmitters, hormones, cytokines, lymphokines, enzymes, biological response modifiers, growth factors, antibodies and trophic factors.

4. The device according to claim 3, wherein the membrane is connected to a chamber top at one end and a chamber bottom at the other end.

5. The device of claim 4, wherein the ends comprise a plug.

6. The device of claim 5, wherein the plug comprises glue.

7. The device according to claim 6, wherein the membrane comprises at least one biocompatible semi-permeable layer across which the biologically active factor is passed through from the chamber into its surroundings.

8. The device according to claim 7, wherein the membrane is made up of a material selected from a group consisting of polyacrylates including acrylic copolymers, polyvinylidenes, polyvinyl chloride copolymers, polyurethanes, polystyrenes, polyamides, cellulose acetates, cellulose nitrates, polysulfones including polyether sulfones, polyphosphazenes, polyacrylnitriles, poly(acrylonitrile/co-vinyl chloride), polytetrafluorethylene, and derivatives, copolymers, and mixtures thereof.

9. The device according to claim 2, further comprising a plurality of distance means.

10. The device according to claim 9, wherein the plurality of distance means are placed within the chamber in a regular pattern or an irregular pattern.

11. The device according to claim 10, wherein at least one of the plurality of distance means comprises the support means.

12. The device according to claim 11, further comprising a connecting means for connecting the device with the distal end of an elongated tether.

13. The device according to claim 9, wherein ratio of diameter of the distance means having circular cross-section relative to diameter of the chamber having circular cross section is in the range of approximately 1:5 to close to 1:1.

14. The device according to claim 9, wherein the thickness of the membrane is in the range of approximately 50-200 pm.

15. The device according to claim 9, wherein the device is an elongated cylindrical capsule with a plug in each end.

16. The device according to claim 7, wherein said biologically active factor is passed through from the chamber into the central nervous system.

* * * * *